United States Patent
Nassivera et al.

(10) Patent No.: US 10,959,922 B2
(45) Date of Patent: Mar. 30, 2021

(54) SILICA-BASED ANTIMICROBIAL ORAL COMPOSITIONS

(71) Applicant: Evonik Operations GmbH, Essen (DE)

(72) Inventors: Terry Nassivera, Gambrills, MD (US); Karl Gallis, Perryville, MD (US); Eric Lundquist, North Wales, PA (US); Linda Mauller, Earleville, MD (US)

(73) Assignee: Evonik Operations GmbH, Essen (DE)

( * ) Notice: Subject to any disclaimer, the term of this patent is extended or adjusted under 35 U.S.C. 154(b) by 394 days.

(21) Appl. No.: 15/275,541

(22) Filed: Sep. 26, 2016

(65) Prior Publication Data

US 2017/0087066 A1    Mar. 30, 2017

Related U.S. Application Data

(60) Provisional application No. 62/233,513, filed on Sep. 28, 2015.

(51) Int. Cl.

| | |
|---|---|
| *A61Q 11/00* | (2006.01) |
| *A61K 8/25* | (2006.01) |
| *A61K 8/02* | (2006.01) |
| *A61K 8/26* | (2006.01) |
| *A61K 8/49* | (2006.01) |
| *A61K 9/14* | (2006.01) |
| *A61K 9/00* | (2006.01) |

(52) U.S. Cl.
CPC .............. *A61K 8/25* (2013.01); *A61K 8/0216* (2013.01); *A61K 8/26* (2013.01); *A61K 8/4926* (2013.01); *A61K 9/0056* (2013.01); *A61K 9/143* (2013.01); *A61Q 11/00* (2013.01); *A61K 2800/28* (2013.01); *A61K 2800/412* (2013.01)

(58) Field of Classification Search
CPC ........ A61K 8/26; A61K 8/4926; A61K 9/143; A61K 8/25; A61K 9/0056; A61K 8/0216; A61K 2800/412; A61K 2800/28; A61P 1/02; A61P 31/04; A61Q 11/00
See application file for complete search history.

(56) References Cited

U.S. PATENT DOCUMENTS

| | | | |
|---|---|---|---|
| 4,224,310 A * | 9/1980 | Shah | A61K 8/19 424/49 |
| 6,663,963 B2 | 12/2003 | Preston et al. | |
| 6,946,119 B2 | 9/2005 | Gallis et al. | |
| 7,255,852 B2 | 8/2007 | Gallis et al. | |
| 7,438,895 B2 | 10/2008 | Gallis | |
| 7,563,451 B2 | 7/2009 | Lin et al. | |
| 8,609,068 B2 | 12/2013 | Hagar et al. | |
| 8,945,517 B2 | 2/2015 | Hagar et al. | |
| 8,980,229 B2 | 3/2015 | Pilch et al. | |
| 2006/0018966 A1 | 1/2006 | Lin et al. | |
| 2011/0236444 A1 | 9/2011 | Darsillo et al. | |
| 2012/0282313 A1 | 11/2012 | Pimenta et al. | |
| 2014/0271749 A1 | 9/2014 | Gallis et al. | |
| 2014/0272012 A1 | 9/2014 | Gallis et al. | |

FOREIGN PATENT DOCUMENTS

| | | |
|---|---|---|
| RU | 2527687 C2 | 9/2014 |
| WO | WO 99/33352 | 7/1999 |
| WO | 2000010528 A1 | 3/2000 |
| WO | 2004073380 A2 | 9/2004 |
| WO | WO 2008/082795 | 7/2008 |
| WO | 2009099453 | 8/2009 |
| WO | 2010068431 A2 | 6/2010 |
| WO | 2011106289 A2 | 9/2011 |
| WO | WO 2013/095370 | 6/2013 |

OTHER PUBLICATIONS

International Search Report and Written Opinion in Application No. PCT/US2016/053756, dated Nov. 21, 2016, 14 pages.
Botelho, M.G., entitled "*The minimum inhibitory concentration of oral antibacterial agents against cariogenic organisms*," Microbios, (2000) vol. 103, pp. 31-41.
Brunauer et al., entitled "*Adsorption of Gases in Multimolecular Layers*," J. Am. Chem. Soc., (1938) vol. 60, pp. 309-319.
Vandekerckhova et al., entitled "*Efficacy on supragingival plaque control of cetylpyridinium chloride in a slow-release dosage form*," J. Clin. Periodontal, (1995) vol. 22, pp. 824-829.
Zhang et al., entitled "*Antibacterial Dental Composites with Chlorhexidine and Mesoporous Silica*," J Dent Res, (2014) 93(12), pp. 1283-1289.
Chemical and Engineering News, 63(5), 27,1985; periodic table (1 page).
PCT International Search Report dated Nov. 21, 2016 corresponding to PCT Application No. PCT/US2016/053756 filed Sep. 26, 2016 (5 pages).

* cited by examiner

*Primary Examiner* — Lezah Roberts

(57) ABSTRACT

Oral compositions containing a carrier, a cationic antimicrobial compound, and a silica and/or silicate material are disclosed. These compositions can provide a controlled release of the antimicrobial compound.

21 Claims, 5 Drawing Sheets

SILICA-BASED ANTIMICROBIAL ORAL COMPOSITIONS

REFERENCE TO RELATED APPLICATION

This application claims the benefit of U.S. Provisional Application Ser. No. 62/233,513, filed on Sep. 28, 2015, the disclosure of which is incorporated herein by reference in its entirety.

BACKGROUND OF THE INVENTION

The present invention is directed to oral compositions containing cationic antimicrobial compounds and silica and/or silicate materials.

It is well known that several antimicrobial quaternary ammonium salts are acceptable for use in the oral environment, for example cetylpyridinium chloride (CPC), benzalkonium chloride (BAC), domiphen chloride, and chlorohexidine. However, in order for these agents to be therapeutically effective, they need to be accessible in the saliva at levels above the minimum inhibitory concentration (MIC). Typically, silica and/or silicate materials have been known to be highly incompatible, resulting in ineffective salivary levels to provide a sufficient antimicrobial benefit. This is due primarily to the well-established interactions between surface silanol groups and quaternary amine moieties. For this reason, previous attempts at improving the antibacterial efficacy of these agents with silica/silicate systems involved making the silica/silicate more compatible through reducing the accessible surface area and/or silanol moieties (i.e., lower surface area), thus decreasing the overall adsorptive capacity for the selected antimicrobial agent. Some drawbacks to these approaches were that the achievable level of compatibility was limited and the resultant silica was very dense and abrasive. Moreover, when certain antimicrobial agents are available at high concentrations, they can have a noticeable off taste, adverse reactions with soft tissues, and can cause enamel staining.

Therefore, it would be beneficial to provide an improved silica/silicate system for the controlled release of antimicrobial agents into an oral cavity. Accordingly, it is to these ends that the present invention is principally directed.

SUMMARY OF THE INVENTION

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

Oral compositions are disclosed and described herein. In accordance with one aspect of this invention, such oral compositions can comprise (i) a carrier, (ii) from about 0.02 to about 2 wt. % of a cationic antimicrobial compound, and (iii) from about 0.1 to about 4.5 wt. % of a silica and/or silicate material. The silica and/or silicate material can be characterized by an average particle size in a range from about 0.1 to about 20 μm, and by a CTAB surface area in a range from about 145 to about 550 $m^2/g$. Moreover, the silica and/or silicate material can have an absorptive capacity of the cationic antimicrobial compound in a range from about 200 to about 400 mg of the cationic antimicrobial compound per gram of the silica and/or silicate material.

In accordance with another aspect of this invention, an oral composition can comprise (a) a carrier and (b) from about 0.15 to about 7 wt. % of treated particles comprising (I) a silica and/or silicate material and (II) a cationic antimicrobial compound. In these and other aspects, the silica and/or silicate material can have an absorptive capacity of the cationic antimicrobial compound in a range from about 200 to about 400 mg of the cationic antimicrobial compound per gram of the silica and/or silicate material, and the treated particles can comprise the cationic antimicrobial compound at an amount in a range from about 50% to about 200% of the absorptive capacity. The absorptive capacity of the silica and/or silicate material is determined using a pH titration test, as described herein.

Processes for producing oral compositions also are provided herein. A representative process can comprise (A) contacting an aqueous slurry of the silica and/or silicate material with the cationic antimicrobial compound to form treated particles, and (B) contacting the treated particles with the carrier to form the oral composition.

Beneficially, the oral compositions encompassed herein can be used to reduce or inhibit microbial growth. Accordingly, a method for reducing or inhibiting microbial growth in an oral cavity of a subject consistent with the present invention can comprise administering (or delivering) an effective amount of any of the oral compositions disclosed herein to the oral cavity of the subject.

Both the foregoing summary and the following detailed description provide examples and are explanatory only. Accordingly, the foregoing summary and the following detailed description should not be considered to be restrictive. Further, features or variations may be provided in addition to those set forth herein. For example, certain aspects may be directed to various feature combinations and sub-combinations described in the detailed description.

DEFINITIONS

Figure 1:
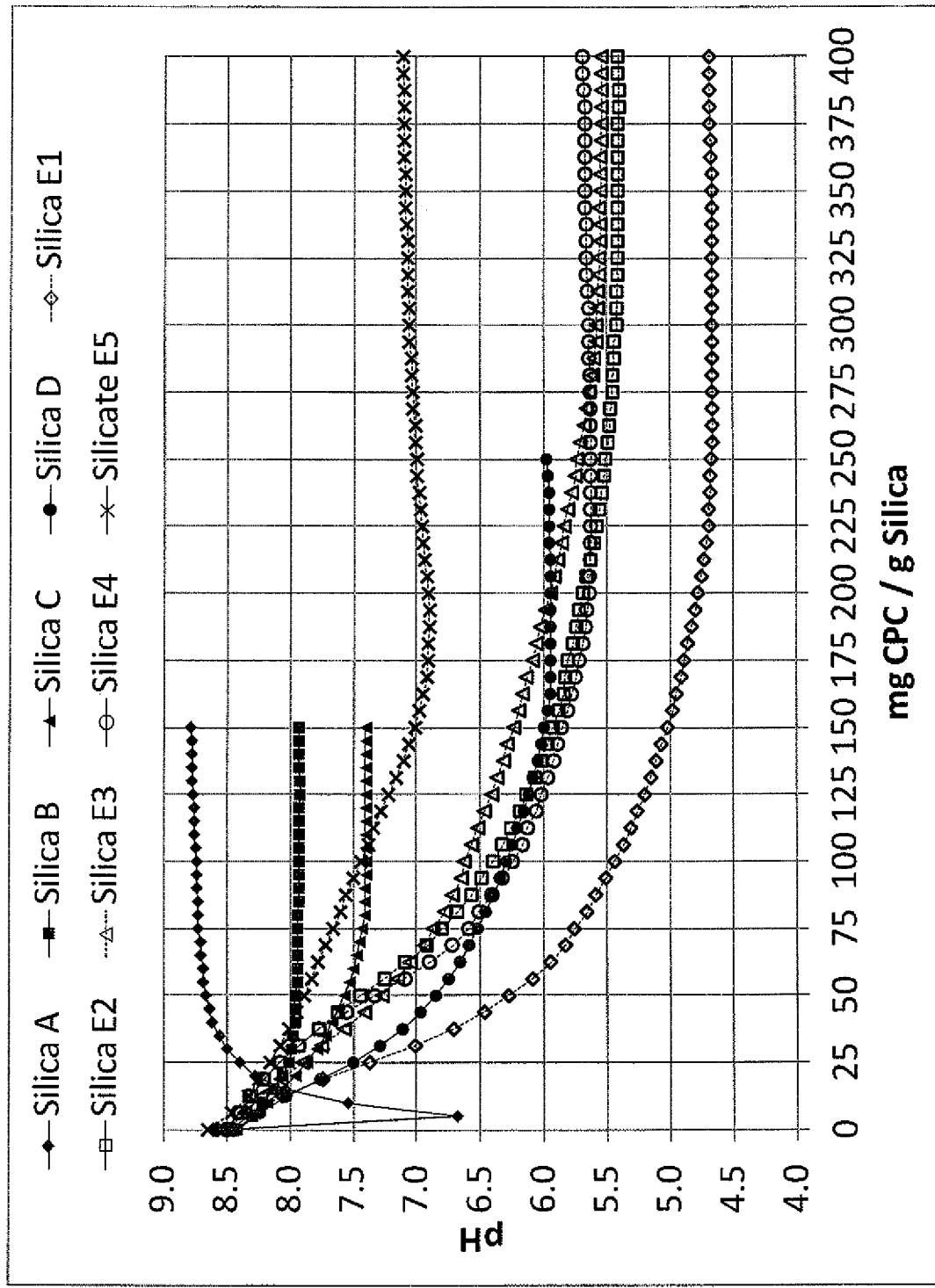
FIG. 1 presents pH profile plots illustrating the pH versus the mg of cetylpyridinium chloride (CPC) per gram of silica/silicate for the materials of Examples 3-11 (comparative silicas A-D and experimental silicas/silicate E1-E5).

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2nd Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter are described such that, within particular aspects, a combination of different features can be envisioned. For each and every aspect and each and every feature disclosed herein, all combinations that do not detrimentally affect the designs, compositions, processes, or methods described herein are contemplated and can be interchanged, with or without explicit description of the particular combination. Accordingly, unless explicitly recited otherwise, any aspect or feature disclosed herein can be combined to describe inventive designs, compositions, processes, or methods consistent with the present disclosure.

While compositions and methods are described herein in terms of "comprising" various components or steps, the compositions and methods can also "consist essentially of" or "consist of" the various components or steps, unless stated otherwise. For example, oral compositions consistent with aspects of the present invention can comprise; alternatively, can consist essentially of; or alternatively, can consist of; (i) a carrier, (ii) a cationic antimicrobial compound, and (iii) a silica and/or silicate material.

The terms "a," "an," and "the" are intended to include plural alternatives, e.g., at least one, unless otherwise specified.

Generally, groups of elements are indicated using the numbering scheme indicated in the version of the periodic table of elements published in *Chemical and Engineering News,* 63(5), 27, 1985. In some instances, a group of elements can be indicated using a common name assigned to the group; for example, alkali metals for Group 1 elements, alkaline earth metals for Group 2 elements, and so forth.

The term "contacting" is used herein to refer to materials or components which can be blended, mixed, slurried, dissolved, reacted, treated, or otherwise contacted or combined in some other manner or by any suitable method. The materials or components can be contacted together in any order, in any manner, and for any length of time, unless otherwise specified.

Although any methods and materials similar or equivalent to those described herein can be used in the practice or testing of the invention, the typical methods and materials are herein described.

All publications and patents mentioned herein are incorporated herein by reference for the purpose of describing and disclosing, for example, the constructs and methodologies that are described in the publications, which might be used in connection with the presently described invention.

Several types of ranges are disclosed in the present invention. When a range of any type is disclosed or claimed, the intent is to disclose or claim individually each possible number that such a range could reasonably encompass, including end points of the range as well as any sub-ranges and combinations of sub-ranges encompassed therein. As a representative example, the CTAB surface area of the silica and/or silicate material can be in certain ranges in various aspects of this invention. By a disclosure that the CTAB surface area can be in a range from about 200 to about 450 $m^2/g$, the intent is to recite that the surface area can be any surface area within the range and, for example, can be equal to about 200, about 250, about 300, about 350, about 400, or about 450 $m^2/g$. Additionally, the surface area can be within any range from about 200 to about 450 $m^2/g$ (for example, from about 250 to about 350 $m^2/g$), and this also includes any combination of ranges between about 200 and about 450 $m^2/g$ (for example, the surface area can be in a range from about 200 to about 300 $m^2/g$ or from about 350 to about 450 $m^2/g$). Likewise, all other ranges disclosed herein should be interpreted in a manner similar to this example.

DETAILED DESCRIPTION OF THE INVENTION

Disclosed herein are oral compositions containing silica and/or silicate materials, methods for producing the oral compositions, and methods of using the oral compositions to reduce microbial growth in an oral cavity of a subject. Also disclosed herein are oral compositions containing specific silica and/or silicate materials, and related methods of use, such that the silica and/or silicate materials can absorb the antimicrobial agent, retain the agent while in a static oral composition (e.g., toothpaste, mouthwash, chewing gum, and the like), yet provide an effective controlled release (above the minimum inhibitory concentration, MIC) when introduced into a dynamic environment, such as the oral cavity of a subject where constant salivary flow conditions exist. Unexpectedly, and contrary to conventional wisdom, it was found that typical silica and/or silicate materials used in oral compositions containing antimicrobial agents do not provide the desired controlled release profile. Moreover, and also unexpectedly, it was found that the loading levels of the silica and/or silicate material in the oral composition must be sufficiently low in order to provide the desired release profile.

Oral Compositions

In accordance with an aspect of the present invention, an oral composition can comprise (i) a carrier, (ii) from about 0.02 to about 2 wt. % of a cationic antimicrobial compound, and (iii) from about 0.1 to about 4.5 wt. % of a silica and/or silicate material characterized by an average particle size in a range from about 0.1 to about 20 μm, and by a CTAB surface area in a range from about 145 to about 550 $m^2/g$. In one aspect of this invention, the silica and/or silicate material (characterized by an average particle size in a range from about 0.1 to about 20 μm, and by a CTAB surface area in a range from about 145 to about 550 $m^2/g$) can comprise a silica material (one or more than one), while in another aspect, the silica and/or silicate material can comprise a silicate material (one or more than one). Yet, in another aspect, the silica and/or silicate material can comprise a mixture or combination of a silica material and a silicate material. Accordingly, mixtures or combinations of two or more different silica materials, two or more different silicate materials, or a silica material and a silicate material (each characterized by an average particle size in a range from about 0.1 to about 20 μm, and by a CTAB surface area in a range from about 145 to about 550 $m^2/g$) can be employed in aspects of this invention.

In accordance with another aspect of the present invention, an oral composition can comprise (a) a carrier and (b) from about 0.15 to about 7 wt. % of treated particles comprising (I) a silica and/or silicate material and (II) a cationic antimicrobial compound. The silica and/or silicate material can have an absorptive capacity of the cationic antimicrobial compound in a range from about 200 to about 400 mg of the cationic antimicrobial compound per gram of the silica and/or silicate material, and the treated particles can comprise the cationic antimicrobial compound at an amount in a range from about 50% to about 200% of the absorptive capacity. In one aspect of this invention, the silica and/or silicate material (characterized by an absorptive capacity of the cationic antimicrobial compound in a range from about 200 to about 400 mg of the cationic antimicrobial compound per gram of the silica and/or silicate material) can comprise a silica material (one or more than one), while in another aspect, the silica and/or silicate material can comprise a silicate material (one or more than one). Yet, in another aspect, the silica and/or silicate material can comprise a mixture or combination of a silica material and a silicate material. Accordingly, mixtures or combinations of two or more different silica materials, two or more different silicate materials, or a silica material and a silicate material (each characterized by an absorptive capacity of the cationic antimicrobial compound in a range from about 200 to about 400 mg of the cationic antimicrobial compound per gram of the silica and/or silicate material) can be employed in aspects of this invention.

The amount of the treated particles present in the oral compositions generally can range from about 0.15 to about 10 wt. %, based on the total weight of the oral composition. In one aspect, the amount of the treated particles can be in a range from about 0.15 to about 7 wt. %, or from about 0.5 to about 7 wt. %. In another aspect, the amount of the treated particles can be in a range from 0.5 to about 4.5 wt. %, or from about 0.5 to about 4 wt. %. In yet another aspect, the amount of the treated particles can be in a range from about 0.75 to about 6 wt. %, or from about 1 to about 4 wt. %. In still another aspect, the amount of the treated particles can be in a range from about 0.25 to about 3 wt. %, or from about 1 to about 3.5 wt. %. Other appropriate ranges for the weight of the treated particles, based on the total weight of the oral composition, are readily apparent from this disclosure.

Consistent with aspects of this invention, a suitable silica and/or silicate material can be determined by its absorptive capacity for the cationic antimicrobial compound. For instance, the silica and/or silicate material can have an absorptive capacity of the cationic antimicrobial compound in a range from about 200 to about 400 mg of the cationic antimicrobial compound per gram of the silica and/or silicate material. As described herein, the absorptive capacity (in mg of the cationic antimicrobial compound per gram of silica and/or silicate material) is the point at which a suspension of the silica and/or silicate material reaches its saturation point for the particular cationic antimicrobial compound. The cationic antimicrobial compound is progressively added to a suspension of a silica and/or silicate material and the pH profile is monitored until the percentage change in pH is greater than −0.25%, indicating a leveling off of the pH, or the pH moving in the positive direction. This indicates that any further antimicrobial agent addition no longer results in generation of exchanged protons from the silica/silicate surface.

A correction is applied to compensate for the moisture content of the silica and/or silicate material based on the loss on drying (LOD) of the material at 105° C. for 2 hr. For example, if 100 g of a 1 wt. % silica suspension is prepared with a silica having a LOD of 6 wt. %, 1.06 g of the as-received silica would be diluted to 100 g with deionized water. Similarly, a correction to the amount of silica and/or silicate material used in the suspension is adjusted to compensate for the amount of sodium sulfate present.

In one aspect of this invention, the silica and/or silicate material can have an absorptive capacity of the cationic antimicrobial compound in a range from about 175 to about 400 mg of the cationic antimicrobial compound per gram of the silica and/or silicate material. In another aspect, the absorptive capacity can be in a range from about 175 to about 350 mg/g, or from about 175 to about 300 mg/g. Yet, in another aspect, the absorptive capacity can be in a range from about 200 to about 400 mg/g, or from about 200 to about 350 mg/g. In still another aspect, the absorptive capacity can be in a range from about 200 to about 325 mg/g, or from about 210 to about 325 mg/g. Other appropriate ranges for the absorptive capacity of the silica and/or silicate material are readily apparent from this disclosure.

The treated particles present in the oral compositions generally can contain a wide range in the amount of the cationic antimicrobial compound that is present. Typically, the treated particles can comprise the cationic antimicrobial compound at an amount in a range from about 50% to about 200% of the absorptive capacity. Thus, the treated particles can contain a silica and/silicate material that is fully loaded with the cationic antimicrobial compound (100% of the absorptive capacity), less than fully loaded with the cationic antimicrobial compound (e.g., 50-85% of the absorptive capacity), or overloaded with the cationic antimicrobial compound (e.g., 110-175% of the absorptive capacity). In the latter case, the excess cationic antimicrobial compound (>100%) can be loosely bound to a surface of, or associated with, the silica and/or silicate during preparation and drying of the treated particles, but once these overloaded treated particles are contacted with the carrier, it is believed that the excess cationic antimicrobial compound, in many circumstances, will rapidly leave the silica and/silicate material.

In certain aspects, the treated particles can comprise the cationic antimicrobial compound at an amount in a range from about 50% to about 200% of the absorptive capacity. However, in other aspects, the treated particles comprise an amount of the cationic antimicrobial material in other ranges, based on the absorptive capacity, such as from about 50% to about 150%, from about 50% to about 125%, from about 50% to about 100%, from about 50% to about 95%, from about 60% to about 100%, from about 75% to about 150%, from about 75% to about 100%, or from about 75% to about 95%, and the like. Other appropriate ranges for the amount of the cationic antimicrobial compound present with the treated particles, based on the absorptive capacity of the silica and/or silicate material, are readily apparent from this disclosure.

Often, the amount of the cationic antimicrobial compound in any of the oral compositions disclosed herein can fall within a range from about 0.02 to about 2 wt. %, based on the total weight of the oral composition. In some aspects, the amount of the cationic antimicrobial compound can be in a range from about 0.05 to about 2 wt. %; alternatively, from about 0.02 to about 1 wt. %; alternatively, from about 0.05 to about 1 wt. %; alternatively, from about 0.1 to about 1 wt. %; alternatively, from about 0.2 to about 1 wt. %; or alternatively, from about 0.2 to about 0.6 wt. %. Other appropriate ranges for the weight of the cationic antimicrobial compound, based on the total weight of the oral composition, are readily apparent from this disclosure.

The amount of the silica and/or silicate material (total, if more than one) in the oral composition typically falls within a range from about 0.1 to about 4.5 wt. %, or from about 0.5 to about 8 wt. %, such as, for example, from about 0.5 to about 4.5 wt. %, from about 0.5 to about 3 wt. %, from about 1 to about 6 wt. %, from about 1 to about 3 wt. %, from about 0.5 to about 2.5 wt. %, from about 0.1 to about 2 wt. %, or from about 1 to about 2 wt. %. Other appropriate ranges for the weight of the silica and/or silicate material, based on the total weight of the oral composition, are readily apparent from this disclosure. It should be noted that this silica and/or silicate material is (#1) characterized by an average particle size in a range from about 0.1 to about 20 µm, and by a CTAB surface area in a range from about 145 to about 550 m$^2$/g, and/or (#2) characterized by an absorptive capacity of the cationic antimicrobial compound in a range from about 200 to about 400 mg of the cationic antimicrobial compound per gram of the silica and/or silicate material.

As one of skill in the art would readily recognize, in some circumstances, the only silica and/or silicate material in the oral composition is that which is defined by at least one of (#1) the aforementioned particle size and CTAB surface area features and (#2) the aforementioned absorptive capacity of the cationic antimicrobial compound. Thus, in some aspects of this invention, the only silica and/or silicate material in the oral composition is a silica and/or silicate material with these defined attributes.

However, as one of skill in the art also would readily recognize, in some circumstances, it can be beneficial for the oral composition to contain additional silica and/or silicate materials, these additional materials being different from those silica and/or silicate materials with the above-defined attributes (particles size and CTAB surface area, absorptive capacity of the cationic antimicrobial compound). Thus, in some aspects of this invention, the oral composition can further comprise a silica and/or silicate material that is different from the silica and/or silicate material characterized by an average particle size in a range from about 0.1 to about 20 µm and a CTAB surface area in a range from about 145 to about 550 m$^2$/g, and/or different from the silica and/or silicate material characterized by an absorptive capacity of the cationic antimicrobial compound in a range from about 200 to about 400 mg of the cationic antimicrobial compound per gram of the silica and/or silicate material.

For instance, oral composition consistent with certain aspects of this invention can further contain from about 1 to about 35 wt. %, from about 5 to about 25 wt. %, or from about 5 to about 15 wt. %, of an abrasive silica material characterized by a CTAB surface area in a range from about 1 to about 60 m$^2$/g, from about 1 to about 50 m$^2$/g, from about 1 to about 35 m$^2$/g, or from about 2 to about 50 m$^2$/g. Additionally or alternatively, the abrasive silica material can be characterized by a relatively low absorptive capacity of the cationic antimicrobial compound, often in a range from about 2 to about 100 mg, from about 3 to about 50 mg, or from about 5 to about 40 mg, of the cationic antimicrobial compound per gram of the abrasive silica material. The abrasive silica material can have any suitable average particle size (d50), for instance, from about 0.1 to about 20, from about 0.5 to about 10, or from about 1.5 to about 7 µm.

One component of the oral composition is a cationic antimicrobial compound. Any suitable cationic antimicrobial compound can be used, illustrative and non-limiting examples of which include cetylpyridinium chloride (CPC), benzalkonium chloride (BAC), domiphen bromide, chlorhexidine, and the like, as well as any mixture or combination thereof. In some aspects of this invention, the cationic antimicrobial compound can comprise cetylpyridinium chloride (CPC); alternatively, benzalkonium chloride (BAC); alternatively, domiphen bromide; or alternatively, chlorhexidine. In other aspects of this invention, the cationic antimicrobial compound can comprise any suitable antimicrobial quaternary ammonium compound, illustrative and non-limiting examples of which include cetylpyridinium chloride (CPC), benzalkonium chloride (BAC), and the like, as well as combinations thereof.

Another component of the oral composition is the silica and/or silicate material. The silica and/or silicate material contemplated herein can comprise any suitable silica and/or silicate material, non-limiting examples of which can include silica gels, fumed silicas, precipitated silicas, colloidal silicas, silicates, alkali metal aluminosilicates, alkaline earth metal-modified alkali metal aluminosilicates, and the like, as well mixtures or combinations thereof.

Representative silica gel materials include those produced by Grace (e.g., SYLOID, SYLODENT) and PQ Corporation (e.g., GASIL, SILCRON, SORBSIL), among others. Representative fumed silica materials include those produced by Cabot Corporation (e.g., CABOSIL) and Evonik Industries (e.g., AEROSIL), among others. Representative precipitated silica materials include those produced by J.M. Huber Corporation (e.g., ZEODENT, ZEOFREE, ZEOTHIX), Grace (e.g., SYLODENT), PQ Corporation (e.g., SORBOSIL), Solvay (e.g., TIXOSIL, ZEOSIL), and Evonik Industries (e.g., SIDENT, SIPERNAT), among others. Representative colloidal silica materials include those produced by W.R. Grace & Co. (e.g., LUDOX), among others. Representative alkali metal aluminosilicate and alkaline earth metal-modified alkali metal aluminosilicate materials include those produced by J.M Huber Corporation (e.g., ZEOLEX, HYDREX, HUBERSORB), among others.

In some aspects, the silica and/or silicate material can comprise any suitable silicate, non-limiting examples of which can include calcium silicate particles, magnesium silicate particles, and the like, as well as combinations thereof. In other aspects, the silica and/or silicate material can comprise any suitable aluminosilicate, non-limiting examples of which can include alkali metal aluminosilicates (e.g., sodium aluminosilicates), alkaline earth metal-modified alkali metal aluminosilicates (e.g., sodium magnesium aluminosilicate), and the like, as well as combinations thereof.

In these and other aspects, any of the suitable silica and/or silicate materials, independently, can be amorphous, can be synthetic, or can be both amorphous and synthetic.

In further aspects, the silica and/or silicate material—for instance, characterized by an absorptive capacity of the cationic antimicrobial compound in a range from about 200 to about 400 mg of the cationic antimicrobial compound per gram of the silica and/or silicate material—also can have any of the characteristics or properties provided hereinbelow, and in any combination.

Typically, the silica and/or silicate material can have a relatively small average particle size. For instance, the silica and/or silicate material can have an average particle size (d50) that often falls within a range from about 0.1 to about 20 µm, such as, for instance, from about 0.1 to about 10, from about 1 to about 20, from about 0.5 to about 20, from about 0.5 to about 10, from about 1 to about 10, from about 2 to about 10, from about 0.5 to about 6, from about 1.5 to about 7, from about 1.5 to about 6, or from about 2 to about 6 µm, and the like. Other appropriate ranges for the average particle size are readily apparent from this disclosure.

In general, the silica and/or silicate material can have a relatively high CTAB surface area. In one aspect, for instance, the CTAB surface area can be in a range from about 130 to about 650 m$^2$/g, or from about 225 to about 650 m$^2$/g. In another aspect, the CTAB surface area can be in a range from about 145 to about 550 m$^2$/g, or from about 175 to about 550 m$^2$/g. In yet another aspect, the CTAB surface area can be in a range from about 250 to about 550 m$^2$/g, from about 250 to about 450 m²/g, or from about 250 to about 350 m²/g. In still another aspect, the CTAB surface area can be in a range from about 200 to about 450 m²/g, or from about 200 m²/g to about 400 m²/g. Other appropriate ranges for the CTAB surface area are readily apparent from this disclosure.

Likewise, the silica and/or silicate material can have a relatively high BET surface area. The BET surface area of the silica and/or silicate material often falls within a range from about 130 to about 800 m²/g, from about 200 to about 800 m²/g, from about 300 to about 800 m²/g, or from about 300 to about 750 m²/g. In some aspects, the BET surface area can be in a range from about 250 to about 700 m²/g, from about 300 to about 650 m²/g, from about 350 to about 700 m²/g, or from about 375 to about 675 m²/g, and the like. Other appropriate ranges for the BET surface area are readily apparent from this disclosure.

In particular aspects of this invention, the silica and/or silicate materials (and oral compositions) described herein do not require a metal or metal adduct, containing for example, aluminum, zinc, tin, strontium, iron, silver, or copper, and the like. Additionally, in aspects of this invention, the silica and/or silicate materials (and oral compositions) described herein are not modified (covalently) with an organic functionality or with other surface functionalization.

Another component of the oral composition is the carrier. Generally, the carrier can comprise any suitable orally acceptable solid or liquid carrier. For instance, the carrier can comprise water, the carrier can comprise a dentifrice composition, and so forth. As required or beneficial for the particular end-use application, the oral composition can contain any suitable additive or additives, non-limiting examples of which can include a humectant, a binder, a flavoring agent, an anti-cavity agent, a colorant, a sweetener, a surfactant, a thickener, or a preservative, and the like, as well as any combination thereof.

The form of the oral composition is not particularly limited, provided that the form is suitable for use in an oral cavity of a human or other mammal. Illustrative examples of forms or end-use products for the oral composition can include, but are not limited to, a mouthwash, a mouth rinse, a mouth spray, a chewing gum, a breath strip, a lozenge, a candy, a tablet, a mint, a toothpaste, a gel, an edible film, or a whitening strip, and the like. Other uses or applications for the oral compositions described herein are readily apparent from this disclosure.

Consistent with aspects of this invention, the oral compositions described herein can be oral compositions configured for, designed for, made for, or used in, the sustained or controlled release of the cationic antimicrobial compound, for instance, in an oral cavity of a subject.

Processes for Preparing Oral Compositions

Processes for preparing oral compositions are disclosed and described herein. Such processes to prepare oral compositions consistent with this invention can comprise (A) contacting an aqueous slurry of the silica and/or silicate material with the cationic antimicrobial compound to form treated particles, and (B) contacting the treated particles with the carrier to form the oral composition.

Generally, the features of the processes (e.g., the characteristics of the oral composition, the characteristics of the silica and/or silicate material, the cationic antimicrobial compound, the conditions under which all the components are contacted and the oral composition is formed, among others) are independently described herein and these features can be combined in any combination to further describe the disclosed processes. For example, the silica and/or silicate material can be characterized by any average particle size disclosed herein, any BET surface area disclosed herein, any CTAB surface area disclosed herein, and any absorptive capacity disclosed herein. The processes disclosed herein can be conducted in any suitable apparatus, such as a container or vessel with a mixing device, or a stirred tank.

Moreover, other process steps can be conducted before, during, and/or after any of the steps listed in the disclosed processes, unless stated otherwise. Additionally, oral compositions produced in accordance with any of the disclosed processes are within the scope of this disclosure and are encompassed herein.

The cationic antimicrobial compound can be contacted with the silica and/or silicate material at a variety of temperature and time periods. For instance, the temperature can be in a range from about 10° C. to about 80° C.; alternatively, from about 10° C. to about 70° C.; alternatively, from about 10° C. to about 60° C.; alternatively, from about 20° C. to about 80° C.; alternatively, from about 20° C. to about 60° C.; alternatively, from about 20° C. to about 50° C.; or alternatively, from about 25° C. to about 75° C. In these and other aspects, these temperature ranges also are meant to encompass circumstances where the process is conducted at a series of different temperatures (e.g., an initial temperature, a final temperature), instead of at a single fixed temperature, falling within the respective ranges. For instance, the cationic antimicrobial compound and the silica and/or silicate material can be contacted initially at a lower temperature, and subsequently, the temperature can be increased to a higher, final temperature.

The duration of the step of contacting the cationic antimicrobial compound with at least one of a silica material and a silicate material is not limited to any particular period of time. Hence, this step can be conducted, for example, in a time period ranging from as little as 15-30 seconds to as long as 24-48 hours, or more. The appropriate contacting time can depend upon, for example, the initial/final temperature, and the percent solids in the aqueous slurry, among other variables. Generally, however, the contacting step can be conducted in a time period that can be in a range from about 15 sec to about 48 hr, such as, for example, from about 1 min to about 24 hr, from about 1 min to about 8 hr, from about 15 min to about 6 hr, from about 5 min to about 2 hr, or from about 30 min to about 2 hr. Other conditions sufficient for conducting the processes described herein are readily apparent from this disclosure.

After the treated particles have been formed in step (A), the treated particles can be dried using any suitable technique, a representative example of which is spray drying. Additionally or alternatively, the processes to produce the oral composition can further comprise a step of wet milling the treated particles, if desired. A bead milling process can be employed, although the wet milling step is not limited thereto. Additionally or alternatively, the processes to produce the oral compositions can further comprise a step of dry milling the treated particles, if desired. A hammer milling process can be employed, although the dry milling step is not limited thereto.

In step (B), the treated particles can be contacted with the carrier to form the oral composition. For instance, an aqueous slurry of the treated particles can be contacted with the carrier in step (B), or alternatively, treated particles that have been dried can be contacted with the carrier in step (B). Regardless, the treated particles can be contacted with the carrier at a variety of temperature and time periods, such as described herein for step (A).

Reducing or Inhibiting Microbial Growth

In accordance with aspects of the present invention, a method of reducing or inhibiting microbial growth in an oral cavity of a subject in need thereof is provided. This method can comprise administering (or delivering) a therapeutically effective amount of any of the oral compositions disclosed herein to the oral cavity of the subject.

As used herein, the term "subject" refers generally to any species of mammal. A mammal encompasses a primate, human, rodent, canine, feline, bovine, ovine, equine, swine, caprine, and the like, but is not limited thereto. Often, the "subject" is a human subject.

The phrase "effective amount" or "therapeutically effective amount" of an oral composition refers to an amount of the composition to be administered to the subject in need thereof. The effective amount can vary based on the particular dosage form of the composition (e.g., mouthwash versus toothpaste versus chewing gum), amount of the silica and/or silicate material in the composition, amount of the antimicrobial compound in the composition, and the like, among numerous other factors. While the suitable effective amount can vary as discussed, often the effective amount of the oral composition can range from about 0.25 to about 25 grams; alternatively, from about 0.25 to about 2 grams; alternatively, from about 0.5 to about 5 grams; alternatively, from about 10 to about 20 grams; or alternatively, from about 5 to about 15 grams. Other appropriate ranges for effective amount of the oral composition are readily apparent from this disclosure.

In some aspects of this invention, the effective amount can be an amount sufficient for a controlled release of at least 1 ppm of the cationic antimicrobial compound (ppm based on weight of contents in the oral cavity, such as saliva) for any suitable controlled release time period. The controlled release time period often can be at least about 15 min, at least about 30 min, at least about 1 hr, or at least about 2 hr, and typical ranges of controlled release time periods can include, but are not limited to, from about 15 min to about 12 hr, from about 30 min to about 8 hr, from about 30 min to about 3 hr, from about 2 hr to about 15 hr, and the like.

EXAMPLES

The invention is further illustrated by the following examples, which are not to be construed in any way as imposing limitations to the scope of this invention. Various other aspects, embodiments, modifications, and equivalents thereof which, after reading the description herein, may suggest themselves to one of ordinary skill in the art without departing from the spirit of the present invention or the scope of the appended claims.

The average particle size, or d50 or median particle size, refers to the particle size for which 50% of the sample has a smaller size and 50% of the sample has a larger size. Average particle size was determined via the laser diffraction method using a Horiba LA 300 instrument.

The BET surface areas disclosed herein were determined in accordance with the BET nitrogen adsorption method of Brunaur et al., J. Am. Chem. Soc., 60, 309 (1938), which is well known to those of skill in the art.

CTAB surface areas disclosed herein were determined by absorption of CTAB (cetyltrimethylammonium bromide) on the silica/silicate surface, the excess separated by centrifugation and the quantity determined by titration with sodium lauryl sulfate using a surfactant electrode. Specifically, about 0.5 grams of the silica/silicate material were placed in a 250-mL beaker with 100 mL CTAB solution (5.5 g/L), mixed on an electric stir plate for 1 hour, then centrifuged for 30 min at 10,000 rpm. One mL of 10% Triton X-100 was added to 5 mL of the clear supernatant in a 100-mL beaker. The pH was adjusted to 3-3.5 with 0.1 N HCl and the specimen was titrated with 0.01 M sodium lauryl sulfate using a surfactant electrode (Brinkmann SUR1501-DL) to determine the endpoint.

Examples 1-2

Particle Retentions Studies

Because particle retention is an important parameter for providing effective controlled release in applications where retention is not inherent, studies were conducted to determine the amount of silica that typically can be retained in the oral cavity. Although this level of retention may be altered through changes to the particle affinity to the hard tissues, soft tissues and biofilms of the oral cavity through surface modification with metal ions, quaternary ammonium species, bioadhesive polymers, etc., these experiments were viewed as a good baseline for the levels needed in order to provide effective release of the adsorbed antimicrobial agent.

In this study, a master 20 wt. % aqueous slurry of the desired silica was made using deionized water and one gram aliquots were distributed into clean pre-weighed fifteen milliliter tubes (200 mg silica). Seven subjects (varying in age and gender, six male and one female) each took a one gram aliquot of the slurry, agitated it to make sure it was fully suspended, poured it into their mouth, and brushed their teeth as usual for one minute, taking care not to ingest any of the contents. The empty tubes were then reweighed to determine the weight of actual slurry used by each participant for each silica sample. The subjects then expectorated the contents of their mouth into a dry and pre-weighed crucible. The subjects were then given five milliliters of deionized water to rinse their mouth, and expectorated this rinse into the same crucible. These crucibles and three controls, which contained a one gram aliquot of the original slurry and five milliliters of rinse water, were placed in a muffle furnace and calcined at 700° C. overnight to remove any introduced organic matter. The furnace was then turned off and once cool, the crucibles were collected and placed in a 100° C. oven until they were ready to be reweighed. The average difference in weight for the three controls was determined and used to determine the quantity of silica per gram of slurry. This value was then used along with the amounts of slurry utilized by each participant to determine a theoretical amount of silica utilized in their test. The difference in weight for the crucibles of the seven participants was then compared to this theoretical amount to calculate the quantity of silica retained as a percentage. These seven values were then used to determine the average amount of each silica sample that was retained in the mouth after brushing.

This experimental protocol was performed for a standard oral care silica with an average particle size of about 8 μm (Example 1, Table I), and a smaller particle size version of about 3.1 μm (Example 2, Table II). As shown in Table I and Table II, the 8 μm particle size silica of Example 1 had an average retention of about 6.27% (11 mg), while the smaller particle size silica of Example 2 had an increased percent retention of about 10.45% (17 mg). Therefore, it was concluded that 10-20 mg of silica could be retained in the oral cavity, and that potentially more than 20 mg of silica could be retained in the oral cavity if a smaller particle size material than Example 2 was utilized.

Examples 3-11

Absorptive Capacity of the Silica and/or Silicate Material

The ability of various silica/silicate materials to absorb and provide controlled release of a cationic antimicrobial agent at sustained levels above the MIC of that agent was evaluated. For these examples, CPC was chosen, since it is a well-known and effective antimicrobial agent, with some literature indicating that it is more effective than chlorhexidine in-vitro, but suffers from low substantively in the oral cavity which renders it less effective in-vivo.

Table III summarizes the characteristics of the silica/silicate materials that were evaluated. A variety of silica/silicate grades are shown in Table III, ranging from highly CPC compatible (Silica A), several commercially available silica grades commonly used in dentifrice applications (Silica B, Silica C, Silica D), and the experimental materials (Silica E1, Silica E2, Silica E3, Silica E4, Silicate E5) that would be generally regarded as highly incompatible with CPC and other cationic or quaternary ammonium antimicrobial agents.

The resultant pH profile from a titration with CPC was used to determine the absorptive capacity of each particular silica/silicate material shown in Table III, in units of mg of CPC per gram of silica/silicate. The pH profiles were generated by titrating using a 4 wt. % CPC solution. All of the silica/silicate suspensions were adjusted to a pH of ~8.5 with either 0.5M NaOH or 0.5M HCl, to help with consistency of the initial surface chemistry and a more direct comparison. With regards to the lower capacity materials, a 5 wt. % suspension was employed to get better resolution of the end point, while a 1 wt. % suspension was employed for the higher capacity materials to allow for a full pH curve to be completed. In order to get as close to the actual wt. % of silica/silicate in the suspension, the amount of as received silica/silicate used was adjusted to compensate for the amount of free moisture (loss on drying) and sodium sulfate present. The compositions of the suspensions employed are summarized in Table IV (Examples 3-11).

The pH profiles for each of the silica materials for Examples 3-11 are illustrated in FIG. 1, in which the pH is shown as a function of the CPC loading on a mg/g basis, as this takes into account the differences in the amount of silica/silicate employed for each test. The absorptive capacity of each silica/silicate was defined by the pH curve separately, and Table V summarizes the absorptive capacity data. The absorptive capacity (or saturation point) from the pH profile was defined as the point where the % change from the previous point became greater than −0.25% (leveled off, or moving in the positive direction). This would indicate that any additional antimicrobial agent did not result in generation of exchanged protons from the silica/silicate surface or the area immediately surrounding it. As shown in Table V, the absorptive capacities of Silica E1, Silica E2, Silica E3, and Silica E4 were in a range from 200 to 300 mg of CPC per gram of silica material.

Also included in Table V is the quantity of each silica/silicate that would be necessary to hold the amount of CPC that would be in a 1 gram ribbon of toothpaste at a CPC loading of 0.3 wt. % (3 mg CPC total), based on the absorptive capacities established using the pH profile. This data indicates that the silica/silicate materials of Examples 6-11 (Silica D, Silica E1, Silica E2, Silica E3, Silica E4, and Silicate E5) would be capable of retaining all of the available CPC in a 20 mg sample that could be retained in the oral cavity (see Examples 1-2).

Examples 12-32

Sustained Release of a Cationic Antimicrobial Compound from the Silica and/or Silicate Material Leaching studies were undertaken to investigate the release of CPC from the silica/silicate material over time. Based on literature relating to the effectiveness of CPC as an antimicrobial, a MIC of 1 ppm was set as a target. Thus, it was desired to have a composition that could maintain a release profile above this MIC of 1 ppm to provide prolonged antimicrobial efficacy.

A desired amount of silica (on a dry basis) was loaded into a vial, and 0.75 g of a 4 wt. % CPC solution was added. After adding the CPC solution, deionized water was added to bring the total weight of the suspension up to 10 g. One series utilized a weight of silica to give 10 wt. % in the suspension (on a dry basis) to mimic a typical silica loading in toothpaste (Examples 12-17, using Silica A, Silica B, Silica C, Silica D, Silica E1, and Silica E2, respectively), while the other utilized enough to provide 2 wt. %, which would mimic what could be theoretically retained in the mouth (Examples 18-23, using Silica A, Silica B, Silica C, Silica D, Silica E1, and Silica E2, respectively). Each suspension was mixed for fifteen minutes prior to use, then a 1 g aliquot (typical toothpaste ribbon amount) was taken out while mixing and placed into a 45 mL amber centrifuge tube. An initial 3 mL aliquot of deionized water was added to mimic the initial use of the product and the tube was then incubated on a rotating rack at 37° C. for 30 min, then centrifuged at 3900 rpm in a hanging bucket centrifuge. The supernatant was collected and placed to the side and another 30 mL aliquot of deionized water was added to the centrifuge tube. The pellet was suspended and the process was repeated. This was done for a total of five more times to give a total wash of 180 mL after the initial dilution.

Figure 2:
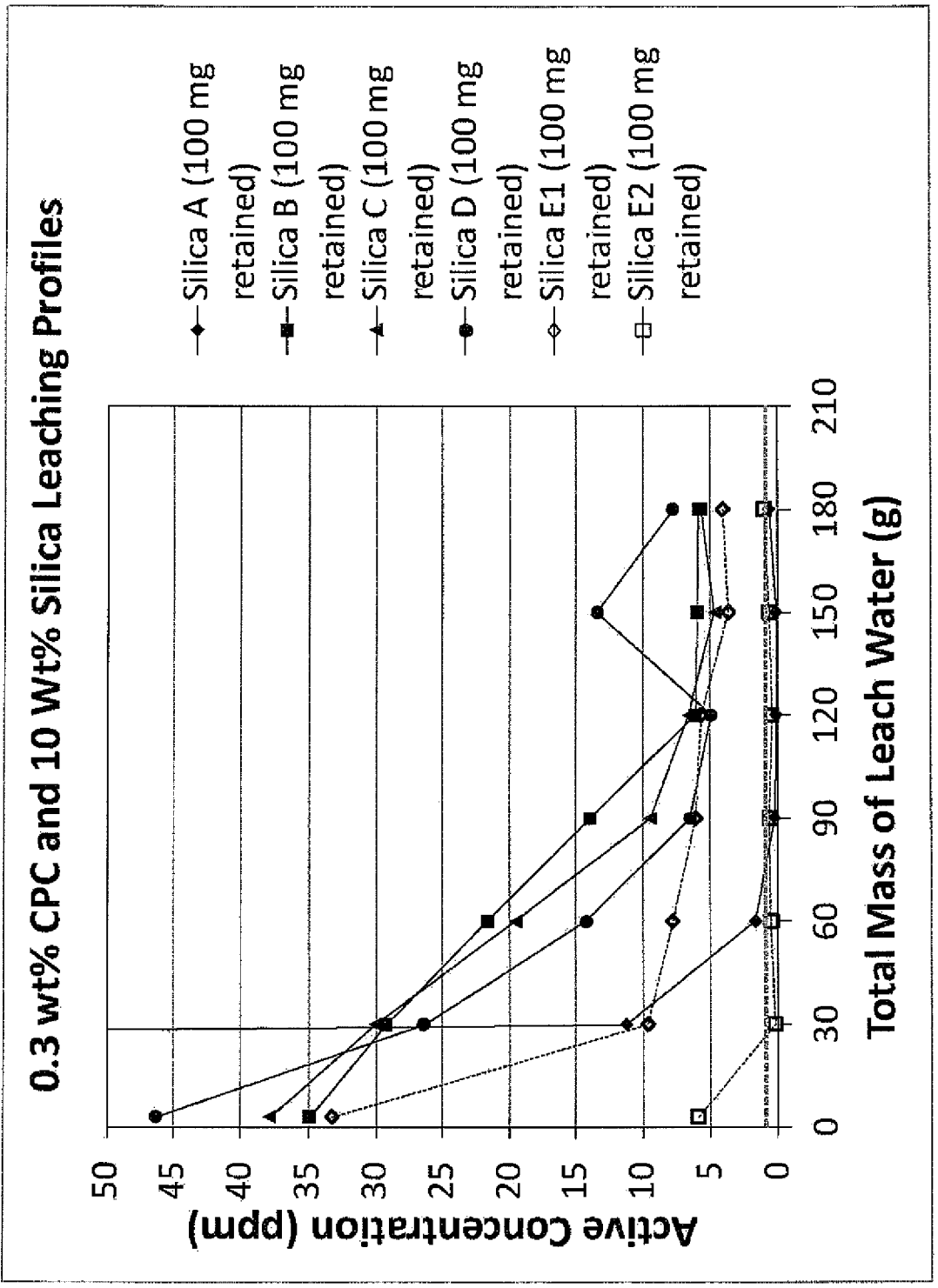
FIG. 2 presents sustained release curves illustrating the concentration in ppm (by weight) of CPC versus the weight of leach water (grams) for the silica materials of Examples 12-17 (comparative silicas A-D and experimental silicas E1-E2) at 10 wt. % silica).

To determine the concentration of CPC that was released in every washing, a LAMBDA 35 UV-VIS spectrometer was utilized at a wavelength of 259 nm and slit width of 0.5 mm and a path length of 1 cm. An initial absorbance vs. concentration calibration curve was generated using CPC solutions ranging from 0 to 200 ppm by weight. Each of the collected supernatants or washes was first run through a 0.22 μm PTFE filter to remove any residual fines or turbidity. The clean supernatant was then measured for its absorbance and the concentration of CPC was calculated. FIG. 2 illustrates the sustained release curves for Examples 12-17 (at 10 wt. % silica) if all 100 mg of silica were retained, and FIG. 3 illustrates the sustained release curves for Examples 18-23 (at 2 wt. % silica) if all 20 mg of silica were retained.

FIG. 2 demonstrates that at normal loading levels and if all 100 mg could be retained, Experimental Silica E1 and Silica E2 (Examples 16-17) showed the worst release profiles, except that of Silica A (Example 12). Silica A could not provide sustained release even at this unrealistic level of retained silica because it has an extremely low adsorptive capacity for CPC and cannot act as an effective reservoir. Therefore, all of the CPC is available and was washed away within the first washing. On the other hand, Silica E2 had the highest capacity for CPC, and because it is utilized at such a high loading level, it is essentially starved for the CPC agent and did not release it into the surrounding solution at a sufficient concentration. The best performers at this unrealistically high level of silica were actually the materials with middle levels of absorptive capacities, since there was enough mass to retain a sufficient quantity and a low enough absorptive capacity to allow for sufficient release.

Figure 3:
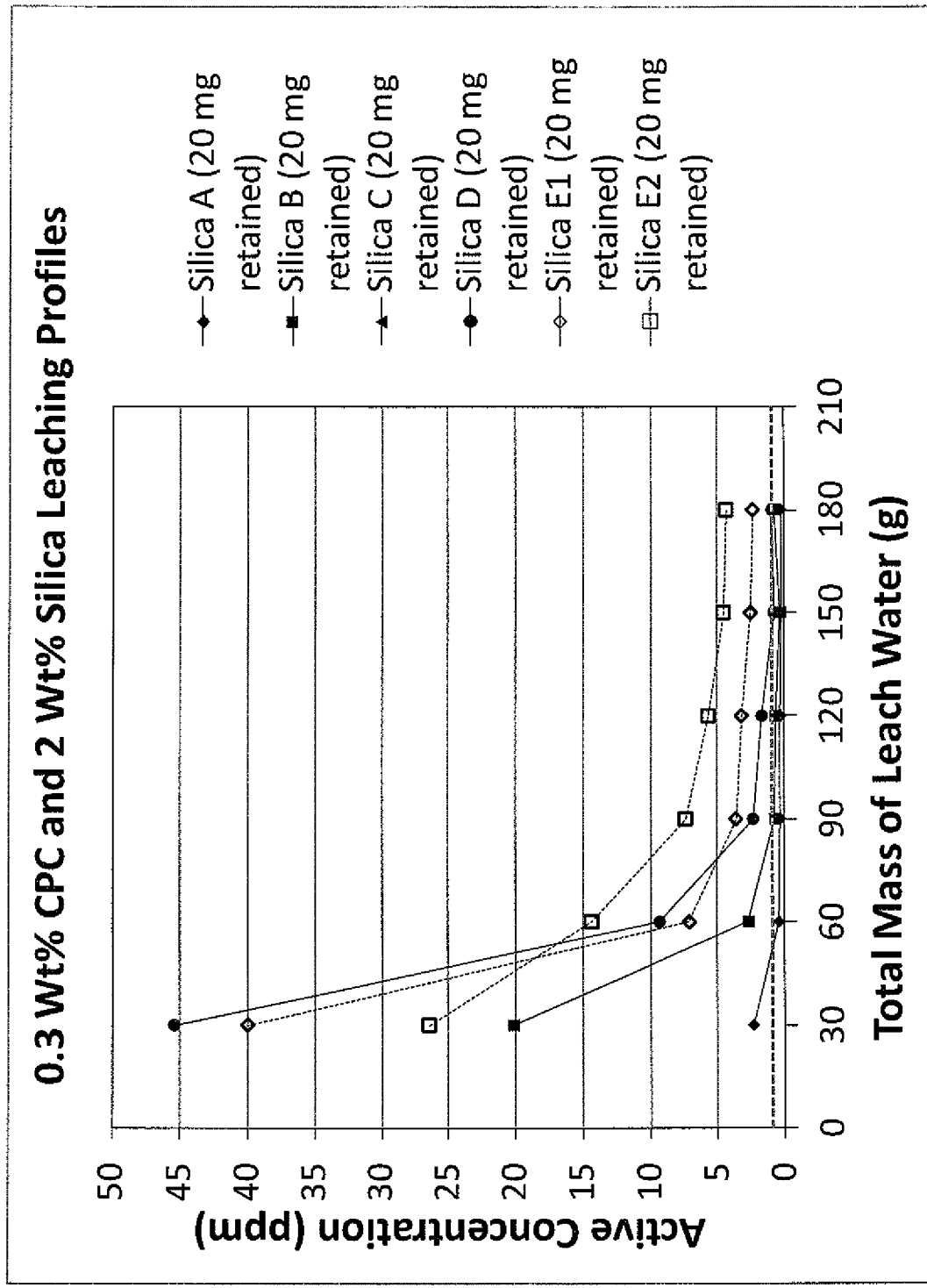
FIG. 3 presents sustained release curves illustrating the concentration in ppm (by weight) of CPC versus the weight of leach water (grams) for the silica materials of Examples 18-23 (comparative silicas A-D and experimental silicas E1-E2) at 2 wt. % silica).

FIG. 3 illustrates how the silica materials perform when the amount of silica retained is a more realistic quantity of 20 mg. Silica A (Example 18) had the worst release profile, once again due to its low absorptive capacity for CPC. The other comparative silica materials (Examples 19-21; Silica B, Silica C, Silica D) did not perform much better, and could only sustain effective levels of greater than 1 ppm of CPC for two or three washings. Unexpectedly, the higher absorptive capacity materials (Examples 22-23; Silica E1, Silica E2) performed extremely well, in which levels of CPC of greater than two to four times the MIC of 1 ppm were achieved for all six washes. At normal salivary flow rates of 0.5-1.0 mL/min, this would equate to the amount of saliva produced over three to six hours.

In addition to these initial experimental materials, three other potential release silica/silicate materials were evaluated for their potential to provide effective CPC release profiles. Silica E3 was a very high CPC absorptive capacity silica, Silica E4 was also a relatively high CPC absorptive capacity silica (made via the processes described in U.S. Pat. Nos. 8,945,517 and 8,609,068, incorporated herein by reference in their entirety), and Silicate E5 was an aluminosilicate with a relatively high CPC absorptive capacity employed to investigate the ability of metal silicates to deliver similar performance to silicas. These three materials were studied in a similar manner to Silica E1 and Silica E2, but some fundamental changes to the leaching procedure were necessary due to equipment changes, the desire to run at a pH of 7.0, and the unexpected incompatibility of a new batch of micro filters.

Therefore, in this study, a desired amount of silica/silicate (on a dry basis) was loaded into a 45 mL centrifuge tube, and 3 g of a 4 wt. % CPC solution was added. After adding the CPC solution, a pH 7.0 phosphate buffer solution made with ultrapure water was added to bring the total weight of the suspension up to 40 g. This series utilized a weight of silica/silicate to give 2 wt. % in the suspension (0.8 g on a dry basis) to mimic what could be theoretically retained in the mouth (Examples 24-26, using Silica E3, Silica E4, and Silicate E5, respectively). In addition, to act as a negative control, a 2 wt. % suspension of Silica E3 was made using no CPC (Example 27), and this was analyzed identically to the CPC containing suspensions.

Each suspension was mixed for at least fifteen minutes prior to use, then a 1 g aliquot (typical toothpaste ribbon amount) was taken out while mixing and placed into a 45 mL centrifuge tube for the repetitive leaching study. The remaining suspension was centrifuged at 5000 rpm for 15 minutes and the supernatant was collected and centrifuged again at 5000 rpm for 15 minutes to remove any remaining small particles. The supernatant generated was collected to act as the point of initial use of the product. The tube containing the 1 g aliquot was centrifuged at 5000 rpm for 15 minutes and the supernatant was discarded. The pellets formed were then re-suspended using 30 mL of pH 7.0 phosphate buffer and incubated on a rotating rack at 40° C. for 15 min, then centrifuged at 5000 rpm for 15 minutes and the supernatant was collected and centrifuged again at 5000 rpm for 15 minutes to remove any fines. The supernatant was collected and placed to the side and another 30 mL aliquot of pH 7.0 phosphate buffer was added to the centrifuge tube. The pellet was suspended and the process was repeated. This was done for a total of 18 more times to give a total wash of 570 mL after the initial dilution.

Figure 4:
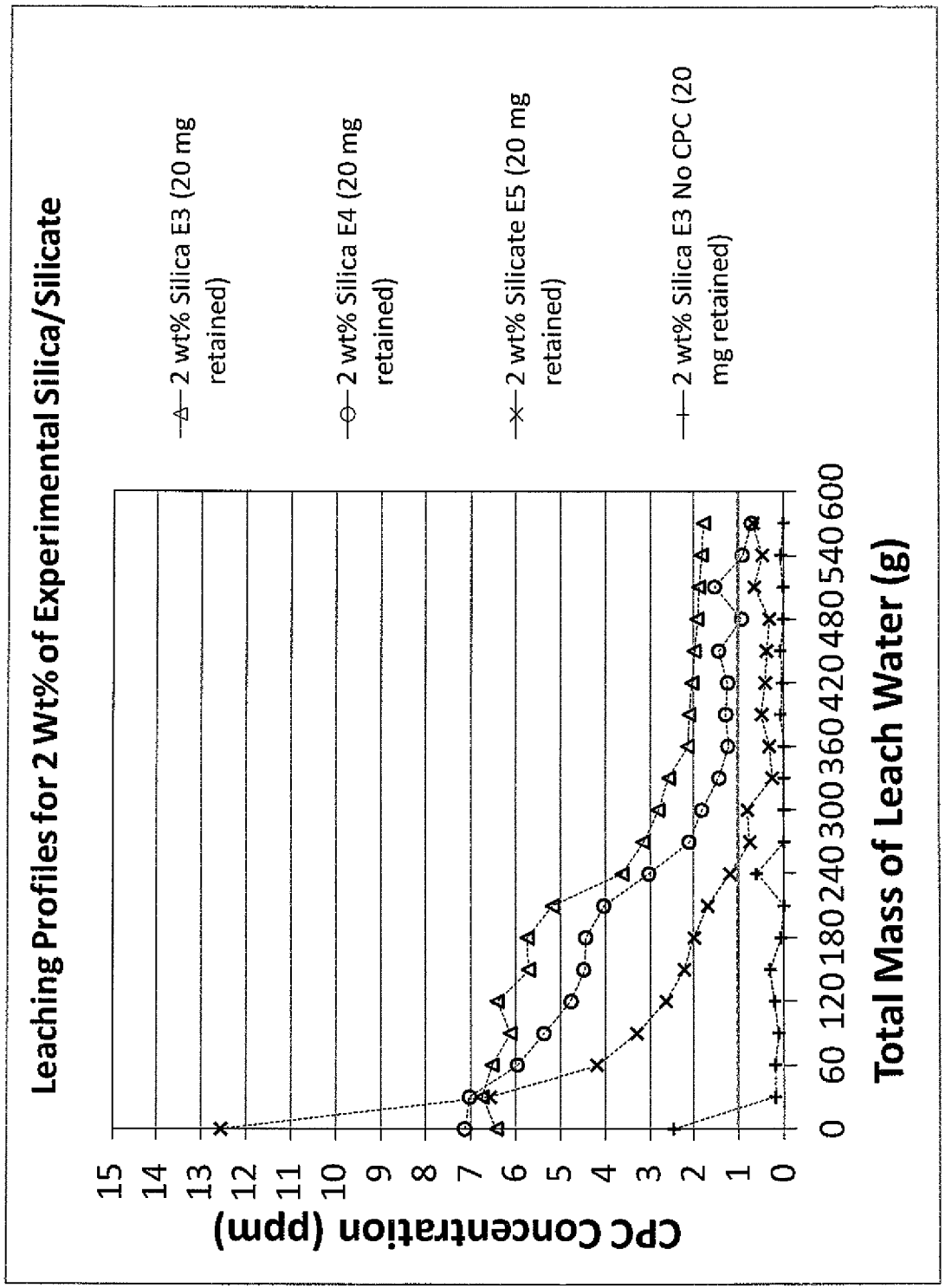
FIG. 4 presents sustained release curves illustrating the concentration in ppm (by weight) of CPC versus the weight of leach water (grams) for the silica/silicate materials of Examples 24-27 (experimental silica/silicate materials E3-E5 at 2 wt. % silica/silicate, and silica E3 with no CPC).

To determine the concentration of CPC that was released in every washing, a CARY 100 UV-VIS spectrometer was utilized at a wavelength of 259 nm and slit width of 0.5 mm and a path length of 1 cm. An initial absorbance versus. concentration calibration curve was generated using CPC solutions ranging from 0 to 150 ppm by weight. Each of the collected clean supernatants were then measured for their absorbance and the concentration of CPC was calculated from the calibration curve. FIG. 4 illustrates the sustained release curves for Examples 24-27 (at 2 wt. % silica/silicate) if all 20 mg of silica/silicate were retained.

FIG. 4 illustrates how the silica/silicate materials perform when the amount of silica retained is a realistic quantity of 20 mg. Silica E3 (Example 24), with the highest absorptive capacity, performed extremely well, in which levels of CPC of greater than or equal to two times the MIC of 1 ppm were achieved for all nineteen washes. Silica E4 (Example 25) was able to sustain effective levels above the MIC for sixteen washes, but did not appear to be as effective as a release material as that of Silica E3. Silicate E5 (Example 26), although not able to sustain the CPC levels as effectively as Silica E3 and Silica E4, indicated that silicate materials meeting the properties disclosed herein can provide release profiles similar to silicas. At normal salivary flow rates of 0.5-1.0 mL/min, Silica E3 and Silica E4 would sustain effective levels for about eight to sixteen hours.

As shown through the CPC titration work, all silica and silicate materials possess some capacity for these quaternary ammonium agents, therefore the addition of another silica into the system would theoretically compete for the available agent and deplete the release silica. In particular, silica based cleaning and polishing particles ("abrasive" silicas) that would be desirable in many oral formulations may reduce the efficacy of the release silica. Therefore, in addition to these initial studies, work was conducted to better understand the potential impact of additional silica/silicate materials in the formulation on this release profile.

Therefore, in this study, a relative capacity for CPC on the release silica and different abrasive silicas was determined. This relative capacity was based on the respective CPC capacity and loading level of the silica. The CPC capacity was established following the previously described titration method and the applicable usage level was set at 2 wt. % for the release silica and a specific level based on the relative cleaning ability of the abrasive silica. For example, Silica C would typically be utilized at 20 wt. %, but Silica A and Silica B often can provide equivalent cleaning at 10 wt. %, therefore these levels were utilized. These relative CPC capacities in the formulation were then utilized to determine what percentage of the available CPC would reside on the release silica and what percentage would reside on the abrasive silica. This information was then utilized to generate suspensions with the release silica loaded with depleted levels of CPC. All of this information is summarized in Table VI, including the amount of a 4% CPC solution needed in the 40 g suspension.

A desired amount of release silica (on a dry basis) was loaded into a 45 mL centrifuge tube, and the determined amount of 4 wt. % CPC solution was added. After adding the CPC solution, a pH 7.0 phosphate buffer solution made with ultrapure water was added to bring the total weight of the suspension up to 40 g. This series utilized a weight of release silica to give 2 wt. % in the suspension (0.8 g on a dry basis) to mimic what could be theoretically retained in the mouth (Examples 28-31, using Silica E3, and Silica E3 with depleted CPC levels due to Silica A, Silica B, and Silica C, respectively). In addition, to act as a negative control, a 2 wt. % suspension of Silica E3 was made using no CPC (Example 32), and this was analyzed identically to the CPC containing suspensions.

Each suspension was mixed for at least fifteen minutes prior to use, then a 1 g aliquot (typical toothpaste ribbon amount) was taken out while mixing and placed into a 45 mL centrifuge tube for the repetitive leaching study. The remaining suspension was centrifuged at 5000 rpm for 15 minutes and the supernatant was collected and centrifuged again at 5000 rpm for 15 minutes to remove any fines. The supernatant generated was collected to act as the point of initial use of the product. The tubes containing the 1 g aliquot were centrifuged at 5000 rpm for 15 minutes and the supernatants were discarded. The pellets formed were then re-suspended using 30 mL of pH 7.0 phosphate buffer and incubated on a rotating rack at 40° C. for 15 min, then centrifuged at 5000 rpm for 15 minutes and the supernatant was collected and centrifuged again at 5000 rpm for 15 minutes to remove any fines. The supernatants were collected and placed to the side and another 30 mL aliquot of pH 7.0 phosphate buffer was added to the centrifuge tubes. The pellets were suspended and the process was repeated. This was done for a total of 18 more times to give a total wash of 570 mL after the initial dilution.

Figure 5:
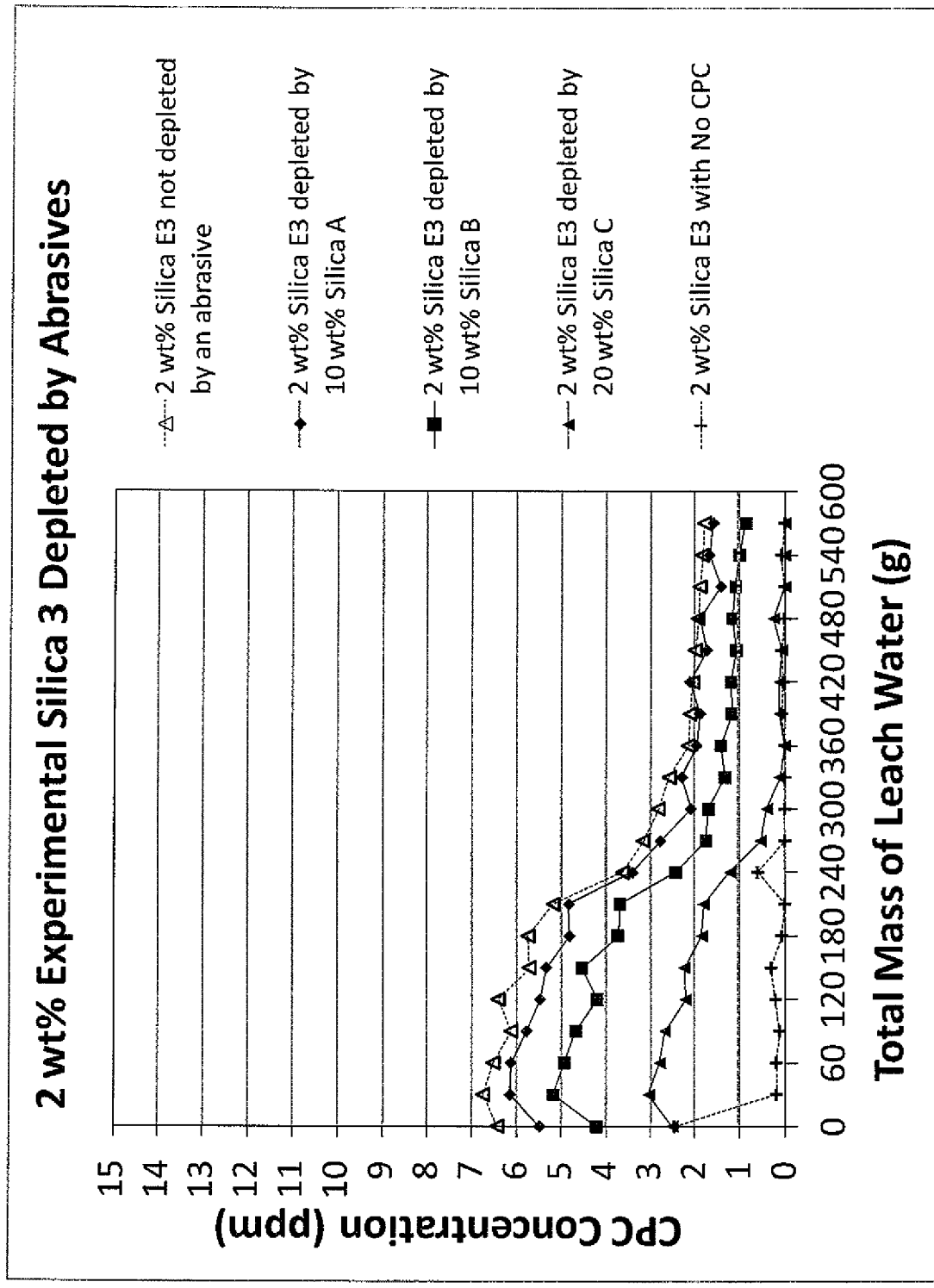
FIG. 5 presents sustained release curves illustrating the concentration in ppm (by weight) of CPC versus the weight of leach water (grams) for the silica/silicate materials of Examples 28-32 (2 wt. % silica E3, silica E3 with silica A, silica E3 with silica B, silica E3 with silica C, and silica E3 with no CPC).

To determine the concentration of CPC that was released in every washing, a CARY 100 UV-VIS spectrometer was utilized at a wavelength of 259 nm and slit width of 0.5 mm. An initial absorbance vs. concentration calibration curve was generated using CPC solutions ranging from 0 to 150 ppm by weight. Each of the collected clean supernatants were then measured for their absorbance and the concentration of CPC was calculated from the calibration curve. FIG. 5 illustrates the sustained release curves for Examples 28-32 (at 2 wt. % silica/silicate) if all 20 mg of silica were retained.

FIG. 5 illustrates how the release silica materials perform when the amount of silica retained is a realistic quantity of 20 mg and when other silica materials can deplete the absorbed CPC. As expected, the un-depleted release silica (Example 28) performed the best, in which levels of CPC of greater than or equal to two times the MIC of 1 ppm were achieved for all nineteen washes. As the release silica was further depleted, the release profile concentrations were lower and fell below the MIC more rapidly. The higher CPC absorptive capacity of cleaning Silica C resulted in significant depletion of CPC from the release silica, thus dropping below the MIC after nine washes (Example 31). The data in FIG. 5 supports the conclusion that a combination of (i) the disclosed release silica/silicate materials in conjunction with (ii) an abrasive silica possessing the lowest CPC absorptive capacity performs the best (for instance, Example 29). It also appears that a relative capacity in use equal to or lower than that of Silica B may be needed to maintain the sustained release over long periods of time.

Contrary to conventional ideology, where high absorptive capacity materials were considered to be unfit for use in these antimicrobial dentifrice applications due to their incompatibility with the agents, these results indicate that, unexpectedly, Silica E1, Silica E2, Silica E3, and Silica E4 (with high absorptive capacities, high CTAB surface areas, etc.) are well-suited materials for effective sustained CPC release, if consideration is given for the actual amount of particles that can be retained in an oral cavity. In addition, Silicate E5 (although lacking sufficient CPC absorptive capacity to provide a release profile comparable to the silica materials), indicates that other metal silicate materials with a sufficient CPC absorptive capacity and/or CTAB surface area also would function similarly. Moreover, in applications where the oral composition is retained in the oral cavity for longer time periods, such as chewing gum, it is believed that even smaller quantities of the treated silica/silicate particles could be used and still provide effective antimicrobial release properties.

TABLE I

Particle retention study data for Example 1 using 8 μm silica

| C1 Subject Number | C2 Mass of silica slurry used (g) | C3 Average empty crucible mass (g) | C4 Average post brushing crucible mass (g) | C5 Average mass of silica in crucible (g) (C3 − C2) | C6 Mass of silica in 1 gram of slurry (g) (C5/C2) | C7 Theoretical mass of silica in slurry used (g) (C2 · 0.17727) | C8 Mass of silica retained (g) (C7 − C5) | C9 Percentage of silica retained CA) (C8/C7) · 100 |
|---|---|---|---|---|---|---|---|---|
| 1 | 1.0033 | 41.56615 | 41.74032 | 0.17417 | — | 0.17786 | 0.00368 | 2.07 |
| 2 | 1.0036 | 44.19611 | 44.36632 | 0.17021 | — | 0.17791 | 0.00770 | 4.33 |
| 3 | 0.9827 | 76.77168 | 76.93341 | 0.16173 | — | 0.17421 | 0.01248 | 7.16 |
| 4 | 0.9976 | 42.94832 | 43.11102 | 0.16269 | — | 0.17685 | 0.01415 | 8.00 |
| 5 | 0.8799 | 41.02345 | 41.15632 | 0.13287 | — | 0.15598 | 0.02311 | 14.82 |
| 6 | 0.9878 | 69.62275 | 69.79492 | 0.17216 | — | 0.17511 | 0.00295 | 1.68 |
| 7 | 0.9879 | 77.21415 | 77.37913 | 0.16499 | — | 0.17513 | 0.01014 | 5.79 |
| Control 1 | 0.9920 | 39.95841 | 40.13213 | 0.17373 | 0.17513 | — | — | — |
| Control 2 | 0.9956 | 76.48821 | 76.66500 | 0.17678 | 0.17756 | — | — | — |
| Control 3 | 0.9805 | 41.40095 | 41.57659 | 0.17563 | 0.17913 | — | — | — |
| Average | | | | | 0.17727 | | 0.01060 | 6.27 |

TABLE II

Particle retention study data for Example 2 using 3.1 μm silica

| C1 Subject Number | C2 Mass of silica slurry used (g) | C3 Average empty crucible mass (g) | C4 Average post brushing crucible mass (g) | C5 Average mass of silica in crucible (g) (C3 − C2) | C6 Mass of silica in 1 gram of slurry (g) (C5/C2) | C7 Theoretical mass of silica in slurry used (g) (C2 · 0.17386) | C8 Mass of silica retained (g) (C7 − C5) | C9 Percentage of silica retained (%) (C8/C7) · 100 |
|---|---|---|---|---|---|---|---|---|
| 1 | 0.95 | 39.92587 | 40.06636 | 0.14049 | — | 0.16516 | 0.02467 | 14.94 |
| 2 | 1.00 | 43.13518 | 43.29871 | 0.16354 | — | 0.17386 | 0.01032 | 5.94 |
| 3 | 0.96 | 42.59649 | 42.73910 | 0.14261 | — | 0.16690 | 0.02429 | 14.55 |
| 4 | 0.93 | 41.01426 | 41.16309 | 0.14882 | — | 0.16169 | 0.01286 | 7.96 |
| 5 | 0.90 | 46.74067 | 46.87676 | 0.13609 | — | 0.15647 | 0.02038 | 13.03 |
| 6 | 0.84 | 69.61910 | 69.75269 | 0.13359 | — | 0.14604 | 0.01245 | 8.53 |
| 7 | 0.98 | 44.61803 | 44.77445 | 0.15641 | — | 0.17038 | 0.01397 | 8.20 |
| Control 1 | 0.97 | 40.66691 | 40.83653 | 0.16963 | 0.17487 | — | — | — |
| Control 2 | 0.99 | 45.75301 | 45.92550 | 0.17249 | 0.17423 | — | — | — |
| Control 3 | 1.00 | 41.47334 | 41.64581 | 0.17247 | 0.17247 | — | — | — |
| Average | | | | | 0.17386 | | 0.01699 | 10.45 |

TABLE III

Characteristics of silica/silicate materials

| Silica/Silicate | A | B | C | D | E1 | E2 | E3 | E4 | E5 |
|---|---|---|---|---|---|---|---|---|---|
| Loss on Drying (%) | 5.95 | 7.15 | 7.25 | 6.55 | 8.20 | 6.20 | 2.25 | 8.05 | 5.45 |
| 325 Mesh Residue (%) | 5.05 | 0.40 | 0.66 | 0.06 | 0.02 | — | 0.10 | — | — |
| BET Surface Area (m²/g) | 1.4 | 35 | 56 | 135 | 430 | 614 | 342 | 381 | 380 |
| CTAB Surface Area (m²/g) | 3 | 29 | 50 | 114 | 293 | 276 | 287 | 151 | 123 |
| Median Particle Size (μm) | 13.21 | 8.31 | 7.93 | 12.50 | 2.62 | 5.22 | 2.51 | 6.17 | 4.30 |
| Na₂SO₄ (%) | <0.35 | 2.00 | 0.66 | 0.51 | 0.51 | 2.00 | 1.50 | — | — |
| Oil Absorption (cc/100 g) | 43 | 50 | 79 | 238 | 256 | 132 | 214 | 106 | 95 |
| Water Absorption (cc/100 g) | 74 | 73.0 | 117 | 281 | 353 | 137 | 243 | 123 | 99 |
| 5% pH | 8.90 | 7.41 | 7.42 | 7.25 | 7.34 | 7.93 | 6.75 | 7.02 | 7.45 |

TABLE IV

Summary of silica/silicate suspensions used in pH profile titrations

| Example | 3 | 4 | 5 | 6 | 7 | 8 | 9 | 10 | 11 |
|---|---|---|---|---|---|---|---|---|---|
| Silica/Silicate | A | B | C | D | E' | E2 | E3 | E4 | E5 |
| Na₂SO₄ (%) | 0.35 | 2.00 | 0.90 | 1.14 | 0.51 | 2.00 | 1.50 | — | — |
| Loss on drying at time of run (%) | 5.95 | 7.15 | 7.25 | 6.55 | 8.20 | 2.90 | 2.25 | 8.05 | 5.45 |
| Desired wt. % of silica/silicate in run | 5.00 | 5.00 | 5.00 | 1.00 | 1.00 | 1.00 | 1.00 | 1.00 | 1.00 |
| Silica/silicate mass needed (g) | 8.00 | 8.00 | 8.00 | 1.60 | 1.60 | 1.60 | 1.60 | 1.60 | 1.60 |
| Mass of silica/silicate used (g) | 8.53 | 8.81 | 8.71 | 1.73 | 1.75 | 1.68 | 1.66 | 1.74 | 1.69 |
| Mass of 0.5M NaOH or 0.5M HCl (g) | 0.02 | 1.20 | 1.20 | 0.28 | 0.18 | 0.00 | 0.35 | 0.05 | 0.05 |
| Wt. % of silica/silicate suspension after pH adjustment | 5.00 | 4.96 | 4.96 | 1.00 | 1.00 | 1.00 | 1.00 | 1.00 | 1.00 |

TABLE V

Summary of absorptive capacity for Examples 3-11

| Example | 3 | 4 | 5 | 6 | 7 | 8 | 9 | 10 | 11 |
|---|---|---|---|---|---|---|---|---|---|
| Silica/Silicate | A | B | C | D | E1 | E2 | E3 | E4 | E5 |
| Absorptive capacity of CPC (mg CPC/g silica/silicate) | 7.5 | 32.5 | 82.5 | 165.6 | 228.1 | 259.4 | 284.4 | 203.1 | 171.9 |

TABLE V-continued

Summary of absorptive capacity for Examples 3-11

| Example | 3 | 4 | 5 | 6 | 7 | 8 | 9 | 10 | 11 |
|---|---|---|---|---|---|---|---|---|---|
| Silica/Silicate | A | B | C | D | E1 | E2 | E3 | E4 | E5 |
| Weight of silica/silicate (mg) needed to adsorb 3 mg of CPC | 400 | 92.3 | 36.4 | 18.1 | 13.2 | 11.6 | 10.6 | 14.8 | 17.5 |

TABLE VI

Summary of CPC depletion from abrasive silicas (cleaning silicas) to determine the impact on release profile

| | Example 28 | Example 29 | Example 30 | Example 31 |
|---|---|---|---|---|
| Release silica | Silica E3 | Silica E3 | Silica E3 | Silica E3 |
| Release silica loading (wt. %) | 2 | 2 | 2 | 2 |
| Release silica mass in 1 g of suspension (g) | 0.02 | 0.02 | 0.02 | 0.02 |
| Release silica absorptive capacity of CPC (mg CPC/g silica) | 284.4 | 284.4 | 284.4 | 284.4 |
| Relative CPC capacity of release silica in 1 g of suspension (mg) | 5.69 | 5.69 | 5.69 | 5.69 |
| Cleaning silica | — | Silica A | Silica B | Silica C |
| Cleaning silica loading (wt. %) | — | 10 | 10 | 20 |
| Cleaning silica mass in 1 g of suspension (g) | — | 0.10 | 0.10 | 0.20 |
| Cleaning silica absorptive capacity of CPC (mg CPC/g silica) | — | 7.5 | 32.5 | 82.5 |
| Relative CPC capacity of cleaning silica in 1 g of suspension (mg) | — | 0.75 | 3.25 | 16.50 |
| Total CPC capacity of release and cleaning silica in 1 g of suspension (mg) | 5.69 | 6.44 | 8.94 | 22.19 |
| Percentage of CPC on release silica (%) | 100 | 88.4 | 63.6 | 25.6 |
| Mass of 4 wt. % CPC solution needed to mimic depletion for 0.3 wt. % CPC suspension | 3.00 | 2.65 | 1.91 | 0.77 |

The invention is described above with reference to numerous aspects and embodiments, and specific examples. Many variations will suggest themselves to those skilled in the art in light of the above detailed description. All such obvious variations are within the full intended scope of the appended claims. Other embodiments of the invention can include, but are not limited to, the following (embodiments are described as "comprising" but, alternatively, can "consist essentially of" or "consist of"):

Embodiment 1

An oral composition comprising (i) a carrier, (ii) from about 0.02 to about 2 wt. % of a cationic antimicrobial compound, and (iii) from about 0.1 to about 4.5 wt. % of a silica and/or silicate material characterized by an average particle size in a range from about 0.1 to about 20 μm, and a CTAB surface area in a range from about 145 to about 550 m²/g.

Embodiment 2

An oral composition comprising (a) a carrier, and (b) from about 0.15 to about 7 wt. % of treated particles comprising (I) a silica and/or silicate material, and (II) a cationic antimicrobial compound; wherein the silica and/or silicate material has an absorptive capacity of the cationic antimicrobial compound in a range from about 200 to about 400 mg of the cationic antimicrobial compound per gram of the silica and/or silicate material; and the treated particles comprise the cationic antimicrobial compound at an amount in a range from about 50% to about 200% of the absorptive capacity.

Embodiment 3

The composition defined in any one of embodiments 1-2, wherein the cationic antimicrobial compound comprises any suitable antimicrobial quaternary ammonium compound or any antimicrobial quaternary ammonium compound disclosed herein, e.g., cetylpyridinium chloride (CPC), benzalkonium chloride (BAC), etc., as well as combinations thereof.

Embodiment 4

The composition defined in any one of embodiments 1-2, wherein the cationic antimicrobial compound comprises cetylpyridinium chloride (CPC).

Embodiment 5

The composition defined in any one of embodiments 1-2, wherein the cationic antimicrobial compound comprises benzalkonium chloride (BAC).

Embodiment 6

The composition defined in any one of embodiments 1-2, wherein the cationic antimicrobial compound comprises domiphen bromide.

Embodiment 7

The composition defined in any one of embodiments 1-2, wherein the cationic antimicrobial compound comprises chlorhexidine.

Embodiment 8

The composition defined in any one of the preceding embodiments, wherein the composition comprises an amount of the cationic antimicrobial compound in any range disclosed herein, e.g., from about 0.02 to about 2 wt. %, from about 0.05 to about 1 wt. %, from about 0.1 to about 1 wt. %, from about 0.2 to about 1 wt. %, from about 0.2 to about 0.6 wt. %, etc.

Embodiment 9

The composition defined in any one of the preceding embodiments, wherein the silica and/or silicate material is characterized by any suitable average particle size, or an average particle size in any range disclosed herein, e.g., from about 0.1 µm to about 20 µm, from about 1 µm to about 20 µm, from about 0.5 µm to about 20 µm, from about 0.5 µm to about 10 µm, from about 1 µm to about 10 µm, from about 2 µm to about 10 µm, from about 0.5 µm to about 6 µm, from about 1.5 µm to about 7 µm, from about 2 µm to about 6 µm, etc.

Embodiment 10

The composition defined in any one of the preceding embodiments, wherein the silica and/or silicate material is characterized by any suitable CTAB surface area, or a CTAB surface area in any range disclosed herein, e.g., from about 145 $m^2/g$ to about 550 $m^2/g$, from about 200 $m^2/g$ to about 450 $m^2/g$, from about 250 $m^2/g$ to about 350 $m^2/g$, etc.

Embodiment 11

The composition defined in any one of the preceding embodiments, wherein the silica and/or silicate material is characterized by any suitable BET surface area, or a BET surface area in any range disclosed herein, e.g., from about 130 $m^2/g$ to about 800 $m^2/g$, from about 200 $m^2/g$ to about 800 $m^2/g$, from about 250 $m^2/g$ to about 700 $m^2/g$, from about 250 $m^2/g$ to about 625 $m^2/g$, etc.

Embodiment 12

The composition defined in any one of the preceding embodiments, wherein the absorptive capacity of the cationic antimicrobial material based on the weight of the silica and/or silicate material is in any suitable range or in any range disclosed herein, e.g., from about 175 to about 400 mg, from about 200 to about 400 mg, from about 200 to about 350 mg, from about 210 to about 325 mg, etc., per gram of the silica and/or silicate material.

Embodiment 13

The composition defined in any one of the preceding embodiments, wherein the treated particles comprise the cationic antimicrobial material in any suitable range or in any range disclosed herein, based on the absorptive capacity, e.g., from about 50% to about 200%, from about 50% to about 150%, from about 75% to about 150%, from about 75% to about 100%, from about 75% to about 95%, etc.

Embodiment 14

The composition defined in any one of the preceding embodiments, wherein the composition comprises an amount of the silica and/or silicate material in any range disclosed herein, e.g., from about 0.5 to about 8 wt. %, from about 0.1 to about 4.5 wt. %, from about 0.5 to about 3 wt. %, from about 1 to about 6 wt. %, from about 1 to about 3 wt. %, from about 0.5 to about 4.5 wt. %, from about 0.1 to about 2 wt. %, from about 1 to about 2 wt. %, etc.

Embodiment 15

The composition defined in any one of embodiments 2-14, wherein the composition comprises an amount of treated particles in any range disclosed herein, e.g., from about 0.5 to about 7 wt. %, from about 0.5 to about 4.5 wt. %, from about 0.75 to about 6 wt. %, from about 1 to about 4 wt. %, from about 0.25 to about 3 wt. %, from about 1 to about 3.5 wt. %, etc.

Embodiment 16

The composition defined in any one of embodiments 1-15, wherein the silica and/or silicate material comprises any suitable silica gel or any silica gel disclosed herein, such as those produced by Grace (e.g., SYLOID, SYLODENT), PQ Corporation (e.g., GASIL, SILCRON, SORBSIL), etc.

Embodiment 17

The composition defined in any one of embodiments 1-15, wherein the silica and/or silicate material comprises any suitable fumed silica or any fumed silica disclosed herein, such as those produced by Cabot Corporation (e.g., CABOSIL), Evonik Industries (e.g., AEROSIL), etc.

Embodiment 18

The composition defined in any one of embodiments 1-15, wherein the silica and/or silicate material comprises any suitable precipitated silica or any precipitated silica disclosed herein, such as those produced by J.M. Huber Corporation (e.g., ZEODENT, ZEOFREE, ZEOTHIX), Grace (e.g., SYLODENT), PQ Corporation (e.g., SORBOSIL), Solvay (e.g., TIXOSIL, ZEOSIL), Evonik Industries (e.g., SIDENT, SIPERNAT), etc.

Embodiment 19

The composition defined in any one of embodiments 1-15, wherein the silica and/or silicate material comprises any suitable colloidal silica or any colloidal silica disclosed herein, such as those produced by W.R. Grace & Co. (e.g., LUDOX), etc.

Embodiment 20

The composition defined in any one of embodiments 1-15, wherein the silica and/or silicate material comprises any suitable aluminosilicate or any aluminosilicate disclosed herein, e.g., alkali metal aluminosilicate particles, alkaline earth metal-modified alkali metal aluminosilicate particles, as well as combinations thereof, such as those produced by J.M Huber Corporation (e.g., ZEOLEX, HYDREX, HUBERSORB), etc.

Embodiment 21

The composition defined in any one of embodiments 1-15, wherein the silica and/or silicate material comprises sodium aluminosilicate particles.

Embodiment 22

The composition defined in any one of embodiments 1-15, wherein the silica and/or silicate material comprises sodium magnesium aluminosilicate particles.

Embodiment 23

The composition defined in any one of embodiments 1-15, wherein the silica and/or silicate material comprises calcium silicate and/or magnesium silicate particles.

Embodiment 24

The composition defined in any one of the preceding embodiments, wherein the silica and/or silicate material is amorphous.

Embodiment 25

The composition defined in any one of the preceding embodiments, wherein the silica and/or silicate material is synthetic.

Embodiment 26

The composition defined in any one of the preceding embodiments, wherein the carrier comprises any suitable orally acceptable solid or liquid carrier, or any orally acceptable solid or liquid carrier disclosed herein, e.g., water, a dentifrice composition, etc.

Embodiment 27

The composition defined in any one of the preceding embodiments, wherein the composition is in any suitable form, or any form disclosed herein, e.g., a mouthwash, a mouth rinse, a mouth spray, a chewing gum, a breath strip, a lozenge, a candy, a tablet, a mint, a toothpaste, a gel, an edible film, a whitening strip, etc.

Embodiment 28

The composition defined in any one of the preceding embodiments, wherein the composition further comprises any suitable additive, or any additive disclosed herein, e.g., a humectant, a binder, a flavoring agent, an anti-cavity agent, a colorant, a sweetener, a surfactant, a thickener, a preservative, etc., as well as combinations thereof.

Embodiment 29

The composition defined in any one of the preceding embodiments, wherein the silica and/or silicate material (or composition) does not contain a metal or metal adduct, e.g., aluminum, zinc, tin, strontium, iron, silver, copper, etc.

Embodiment 30

The composition defined in any one of the preceding embodiments, wherein the silica and/or silicate material is not modified with organic functionality or other surface functionalization.

Embodiment 31

The composition defined in any one of embodiments 1-30, wherein the only silica and/or silicate material in the composition is element (iii) or in the treated particles of element (b).

Embodiment 32

The composition defined in any one of embodiments 1-30, wherein the composition further comprises a silica and/or silicate material different from element (iii) or different from the silica and/or silicate material in the treated particles of element (b).

Embodiment 33

The composition defined in any one of the preceding embodiments, wherein the composition is produced by a process comprising (A) contacting an aqueous slurry of the silica and/or silicate material with the cationic antimicrobial compound to form treated particles; and (B) contacting the treated particles with the carrier to form the composition.

Embodiment 34

The composition defined in embodiment 33, further comprising a step of drying the treated particles after step (A).

Embodiment 35

The composition defined in any one of embodiments 33-34, wherein the silica and/or silicate material is contacted with the cationic antimicrobial compound at any suitable temperature and time period, or any temperature and time period disclosed herein, e.g., from about 10° C. to about 80° C., from about 20° C. to about 60° C., from about 15 sec to about 48 hr, from about 1 min to about 8 hr, from about 5 min to about 2 hr, etc.

Embodiment 36

The composition defined in any one of the preceding embodiments, wherein the composition is an oral composition configured for, designed for, made for, or used in, the sustained or controlled release of the cationic antimicrobial compound, e.g., in an oral cavity of a subject.

Embodiment 37

A method of reducing or inhibiting microbial growth in an oral cavity of a subject, the method comprising administering (or delivering) an effective amount of the composition defined in any one of the preceding embodiments to the oral cavity of the subject.

Embodiment 38

The method defined in embodiment 37, wherein the subject is a mammal.

Embodiment 39

The method defined in embodiment 37, wherein the subject is a human.

Embodiment 40

The method defined in any one of embodiments 37-39, wherein the effective amount is any suitable effective amount, or any effective amount disclosed herein, e.g., from about 0.25 to about 25 grams, from about 0.25 to about 2 grams, from about 10 to about 20 grams, etc.

Embodiment 41

The method defined in any one of embodiments 37-40, wherein the effective amount is an amount sufficient for a controlled release of at least 1 ppm of the cationic antimicrobial compound for any suitable controlled release time period or in any range of controlled release time periods disclosed herein, e.g., from about 15 min to about 12 hr, from about 30 min to about 8 hr, from about 30 min to about 3 hr, etc.

We claim:

1. An oral composition comprising:
   (i) a carrier;
   (ii) from about 0.02 to about 2 wt. % of a cationic antimicrobial compound; and
   (iii) from about 0.5 to 3 wt. % of a silica and/or silicate material characterized by:
      an average particle size in a range from about 0.1 to about 20 μm;
      a CTAB surface area in a range from about 250 to about 350 m$^2$/g; and
      an absorptive capacity of the cationic antimicrobial compound in a range from about 200 to about 400 mg of the cationic antimicrobial compound per gram of the silica and/or silicate material.

2. The composition of claim 1, wherein:
   the silica and/or silicate material comprises a precipitated silica having an absorptive capacity of the cationic antimicrobial compound in a range from about 210 to about 325 mg/g; and
   the cationic antimicrobial compound comprises an antimicrobial quaternary ammonium compound.

3. The composition of claim 1, wherein the silica and/or silicate material comprises an alkali metal aluminosilicate characterized by:
   an average particle size in a range from about 0.5 μm to about 10 μm;
   a CTAB surface area in a range from about 250 m$^2$/g to about 350 m$^2$/g; and
   a BET surface area in a range from about 200 m$^2$/g to about 800 m$^2$/g.

4. The composition of claim 1, wherein the silica and/or silicate material comprises a precipitated silica characterized by:
   an average particle size in a range from about 0.5 μm to about 6 μm; and
   a BET surface area in a range from about 250 m$^2$/g to about 700 m$^2$/g.

5. The composition of claim 4, wherein the cationic antimicrobial compound comprises cetylpyridinium chloride (CPC).

6. The composition of claim 1, wherein:
   the carrier comprises water; and
   the composition comprises from about 0.1 to about 1 wt. % of the cationic antimicrobial compound and from about 0.5 to 3 wt. % of the silica and/or silicate material.

7. The composition of claim 1, wherein:
   the carrier comprises a dentifrice composition; and
   the oral composition comprises from about 0.1 to about 1 wt. % of the cationic antimicrobial compound and from about 0.5 to 3 wt. % of the silica and/or silicate material.

8. The composition of claim 1, wherein the composition is in the form of a mouthwash, a mouth rinse, a mouth spray, a chewing gum, a breath strip, a lozenge, a candy, a tablet, a mint, a toothpaste, a gel, an edible film, or a whitening strip.

9. The composition of claim 1, wherein the composition further comprises an additive comprising a humectant, a binder, a flavoring agent, an anti-cavity agent, a colorant, a sweetener, a surfactant, a thickener, a preservative, or combinations thereof.

10. The composition of claim 1, wherein the composition further comprises an abrasive silica material characterized by:
    a CTAB surface area in a range from about 1 to about 60 m$^2$/g; and
    an absorptive capacity of the cationic antimicrobial compound in a range from about 2 to about 100 mg of the cationic antimicrobial compound per gram of the abrasive silica material.

11. The composition of claim 10, wherein the composition comprises from about 5 to about 25 wt. % of the abrasive silica material.

12. A method of reducing or inhibiting microbial growth in an oral cavity of a subject, the method comprising administering an effective amount of the composition of claim 1 to the oral cavity of the subject.

13. The method of claim 12, wherein:
    the subject is a human; and
    the effective amount is in a range from about 0.25 to about 25 grams.

14. The method of claim 12, wherein:
    the subject is a human; and
    the effective amount is an amount sufficient for a controlled release of at least 1 ppm of the cationic antimicrobial compound for a controlled release time period in a range from about 15 min to about 12 hr.

15. An oral composition comprising:
    (a) a carrier; and
    (b) from about 0.5 to 4.5 wt. % of treated particles comprising:
       (I) a silica and/or silicate material; and
       (II) 0.1 to 1 wt. % of a cationic antimicrobial compound comprising cetylpyridinium chloride; wherein:
    the silica and/or silicate material has an absorptive capacity of the cationic antimicrobial compound in a range from about 200 to about 400 mg of the cationic antimicrobial compound per gram of the silica and/or silicate material; and
    the treated particles comprise the cationic antimicrobial compound at an amount in a range from about 50% to about 200% of the absorptive capacity; and
    the silica and/or silicate material is characterized by:
       an average particle size in a range from about 0.5 μm to about 6 μm;
       a CTAB surface area in a range from about 250 m$^2$/g to about 350 m$^2$/g; and
       a BET surface area in a range from about 250 m$^2$/g to about 700 m$^2$/g.

16. The composition of claim 15, wherein the treated particles comprise the cationic antimicrobial compound at an amount in a range from about 75% to about 150% of the absorptive capacity.

17. The composition of claim 15, wherein:
    the silica and/or silicate material comprises a precipitated silica having an absorptive capacity of the cationic antimicrobial compound in a range from about 210 to about 325 mg/g; and
    the composition comprises from about 1 to 3 wt. % of the precipitated silica.

18. The composition of claim 15, wherein the composition further comprises from about 5 to about 15 wt. % of an abrasive silica material characterized by:
    a CTAB surface area in a range from about 1 to about 35 m$^2$/g; and an absorptive capacity of the cationic antimicrobial compound in a range from about 5 to about 40 mg of the cationic antimicrobial compound per gram of the abrasive silica material.

19. A method of reducing or inhibiting microbial growth in an oral cavity of a subject, the method comprising administering an effective amount of the composition of claim 15 to the oral cavity of the subject; wherein:
   the effective amount is in a range from about 0.25 to about 25 grams; and/or
   the effective amount is an amount sufficient for a controlled release of at least 1 ppm of the cationic antimicrobial compound for a controlled release time period in a range from about 30 min to about 8 hr.

20. The composition of claim 1, wherein said composition is capable of providing a controlled release of at least 1 ppm of the cationic antimicrobial compound for a controlled release time period in a range from about 15 min to about 12 hr.

21. The composition of claim 20, wherein the composition, when the antimicrobial compound is cetylpyridinium chloride and such composition is administered to the oral cavity of a subject, achieves a controlled release of greater or equal to two times the MIC of 1 ppm of the cetylpyridinium chloride for all nineteen washes.

* * * * *